United States Patent [19]
Freund et al.

[11] Patent Number: 5,507,184
[45] Date of Patent: Apr. 16, 1996

[54] PROCESS AND APPARATUS FOR ACTIVATING A TIME GATE IN THE ULTRASONIC TESTING OF MATERIALS USING THE IMPULSE-ECHO SYSTEM

[75] Inventors: Alexander Freund, Wesseling; Ingo Stahl, Pullheim; Norbert Steinhoff, Erftstadt-Liblar; Reinhard Prause, Sankt Augustin, all of Germany

[73] Assignee: Krautkramer GmbH & Co., Germany

[21] Appl. No.: 90,304

[22] Filed: Jul. 12, 1993

[30] Foreign Application Priority Data

Jul. 17, 1992 [DE] Germany ............... 42 23 502.2

[51] Int. Cl.⁶ ........................................... G01N 29/06
[52] U.S. Cl. ................................. 73/611; 73/628
[58] Field of Search ........................... 73/611, 610, 609, 73/613, 622, 625, 628, 644

[56] References Cited

U.S. PATENT DOCUMENTS

| | | | |
|---|---|---|---|
| 3,415,110 | 12/1968 | Cowan | 73/611 |
| 3,599,478 | 8/1971 | Weinbaum | 73/611 |
| 3,741,334 | 6/1973 | Kaule | 73/628 |
| 4,395,911 | 8/1983 | Macecek | 73/622 |
| 4,709,582 | 12/1987 | Besanceney | 73/611 |
| 5,228,343 | 7/1993 | Schoenen et al. | 73/644 |

Primary Examiner—Hezron E. Williams
Assistant Examiner—Rose M. Finley
Attorney, Agent, or Firm—K. S. Cornaby

[57] ABSTRACT

In the process whereby a time gate but especially the time gate for an expected error range 58 in a device by means of which materials are tested by ultra sound according to the impulse echo process involving a test head 20 which emits pulses that impinge diagonally on the surface 28 of a test piece 24, the test head 20 that emits diagonally is firmly connected to a test head 22 from which pulses are emitted vertically. Both test heads emit at given intervals 48, 49 ultra sound impulses and subsequently receive them. The echo signal 50 of the entry of sound of the test head 22 from which pulses emit vertically is utilized to activate the time gate of the test head from which sound is emitted diagonally.

6 Claims, 1 Drawing Sheet

PROCESS AND APPARATUS FOR ACTIVATING A TIME GATE IN THE ULTRASONIC TESTING OF MATERIALS USING THE IMPULSE-ECHO SYSTEM

BACKGROUND OF THE INVENTION

The invention pertains to a process for activating a gate, more particularly a gate in a range where errors are expected in testing materials by the ultrasound method using the pulse echo process. The process incorporates a test head that emits diagonally onto the surface of the material to be tested. The invention pertains also to an apparatus that functions according to this process.

In the procedure of this kind that is already familiar from the publication DE-23 21 699 the input echo is employed for activating the expected error gate of the same test head. This publication demonstrates that such an echo start device tier an expected error gate can only function when the signal of the sound entrance echo is at least of a certain amplitude. Different ways of attaching the device to the surface of the material to be tested cause changes in the echo signal, however, and in addition, variations occur in the height of the signal in the portion of the sound emitted from the surface of the test material. In consequence, activation of the evaluation gate can be delayed to the extent of several ultrasound wave lengths.

Procedures of the above mentioned kind are also familiar from publications OS-41 50 577 and DE-30 17 900 C2. For general reference to this procedure see also the DE-publication "Ultrasonic Testing of Material" by J. and H. Krautkramer, 4th edition.

For test heads from which the impulse is emitted diagonally the procedure that is already familiar and the device that functions according to this procedure have not always led to reproducible results. In test heads of this kind a relatively small and also broad sound input register is frequently present. In consequence, the echo start conditions can not be conclusively realized under practical conditions because on the one hand the strong dynamic can lead to loss of the start incident because the echo remains smaller than a given threshold, for which reason the test is not concluded. On the other hand, by reason of the dynamic and the broad echo signals, the start point for the expected error range changes, for which reason the gate/aperture position varies.

The purpose of the invention is defined by these considerations, its aim being to improve the echo start steering for the aperture/gate position of an expected error range or of another time range in such a way that, for a test head from which the pulse is emitted diagonally, the best possible coordination between transmission of a sound impulse and activation of the time gate, e.g. an expected error range gate, is achieved.

As was demonstrated in procedural tests, this task is solved by a device for activating a time gate but especially an aperture for an expected error range in testing materials according to the impulse echo process; said device incorporates a test head which emits pulses that impinge horizontally on the surface of a test body that is characterized by the test head from which the pulses are emitted vertically and which is firmly connected to a test head on which pulses impinge vertically; said test heads transmit at given intervals ultra sound impulses which are subsequently received; and the echo impulse of the entry of the sound into the test head from which the pulses are emitted vertically is utilized to trigger the time gate of the test head from which the pulses are emitted diagonally.

With reference to the device, it was solved by a process characterized by a test head from which pulses emitted diagonally and a test head from which pulses transmitted in the main vertically are connected firmly together; and they are moveable relative to a test body; the receiver channel of the test head from which pulses are emitted vertically is fitted with a time gate for the input echo; this input echo, if necessary after traversing a time delay switch, is conducted as trigger signal of the time gate for an expected error range of the receiver channel of the test head from which pulses are emitted diagonally.

In essence, the invention is based on evaluating the sound entry display for an additional test head that is connected to the test head from which the pulse is received diagonally. The pulse of this additional test head is essentially vertical. When the ultrasound waves are introduced vertically it is usual to receive a high, narrow signal for the portion of the sound that is reflected at the surface of the test material. For this reason it is possible to tune more finely the starting point for the time gate and, in particular, the gate for the expected error range. The sound input echo for the test head from which the sound is emitted vertically is now introduced in order to determine the instant for activating the expected error gate for the test head from which the pulse is emitted diagonally. In most applications the sound input echo for the test head from which the pulse is emitted vertically is delayed by a given period of time. For devices that function cyclically the delay time is added.

The procedure that is in accord with the invention offers the advantage that the signal of the sound input echo is processed and can be prepared before it is required for activating the expected error gate. By reason of the present state of the technology, however, the entry signal continues to be processed in real-time, and under these conditions evaluation is to say the least difficult. As ultrasonic testing devices normally function cyclically, preparation and time delay for the pulse entry echo can be conducted simply because the processes proceed periodically.

Even though the process is described in the main for activating an expected error gate no limitation to the patent sought is implied. The process can just as well be employed for activating any other time gate, for example, a gate for a variable interference/suppression point, and in this connection reference is made to publication DE 38 22 699 AI. It can also be employed for measuring run time or the like. In place of the concept pulse-echo-process the word pulse-reflection-method is frequently employed since it has the same meaning.

It is normally not necessary to provide a separate test head from which the pulse is emitted vertically exclusively for the echo start of the time gate; instead, test heads which are present any way and from which the pulse is emitted vertically, such as for example test heads for determining the thickness of walls, or heads for ascertaining core faults, can be employed. In order to employ such test heads for the echo start of an expected error range of a test head from which the pulse is emitted diagonally they should impinge on the same surface point as the test head that impinges diagonally. Under these conditions, there occurs in a certain range of the lead advance a proportionality between forward run of the test head from which the pulse is emitted vertically and forward run of the test head from which the pulse is emitted diagonally. For this reason, changes in the forward run of the test head from which the pulse is emitted vertically can easily be transformed into changes in the forward run of the test head from which the pulse is emitted diagonally.

It has proved of great advantage in determining the sound entry echo to take into account in each instance at least the last known echo of the test head from which the pulse is emitted vertically. In devices that function cyclically the time of occurrence of the last known input echo is then incorporated in the event that the input echo of the test head from which the pulse is emitted vertically should fail. In this way the test is not interrupted. In order to obtain in this way the median position for the input echo it is especially advantageous if a roving median range results from the last echo time instants. Determining the gate in the expected error range becomes more stable because of this, which is to say that it wanders back and forth less with every test.

THE DRAWING

Further advantages and characteristics of the invention derive from the remaining claims as well as from the following description of a model of the invention, it being understood that the example described does not limit the protection sought. This example is explained in greater detail with reference to the diagram. In it:

DETAILED DESCRIPTION OF THE DRAWING

Figure 1:
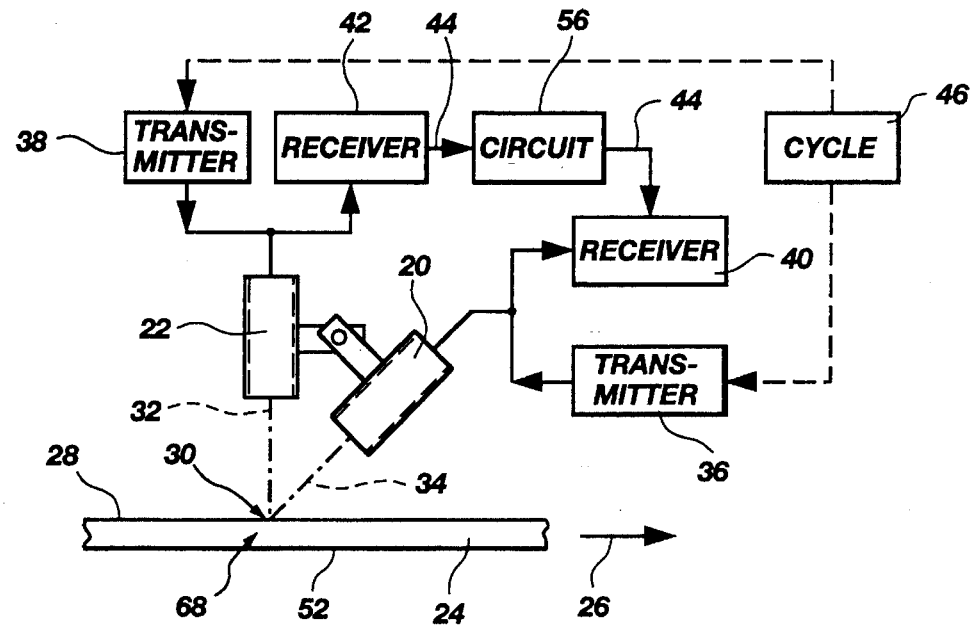
FIG. 1 shows a side view of an ultrasonic testing device that is fitted with two test heads and an electronic system that is schematically represented in block circuitry form.

As is shown in FIG. 1, two test heads 20, 22 are rigidly connected together and moved relative to a test body 24. An arrow 26 is included in the direction of movement; it is intended to indicate movement to the right of the test body 24. The test body in question 24 can be, for example, a pipe which, as is well known, is examined by a rotating test machine. In this case both test heads 20, 22 are arranged in a rotor, and the test body 24 in the form of a pipe is moved axially in arrow direction.

Pulses from the test head 20 impinge diagonally on the surface 28 of the test body 24, whereas the test head 22 is arranged on a norm to the surface 28 so that its pulses impinge vertically on the surface 28. Both test heads 20, 22 are so arranged that their central beams converge at a point 30 on the surface 28. This point 30 is the point of entry of the central beams of both test heads 20, 22 in the test body 24. Coupling both the test heads 20, 22 is effected according to the state of the art, that is, via a water forward run. In this way a considerable portion of the sound energy that is given off at certain instants by both test heads 20, 22 enters the test body 24. By reason of the connecting surface between the coupling medium and the test body 24, a portion of the sound energy is nevertheless reflected. Even for test heads which are constructed identically, this portion is for the test head from which the pulse is emitted vertically 22 disproportionally larger than the portion for the test head from which the pulse is emitted diagonally 20. For this head (20) the reflected portion, proceeding from point 30, proceeds in the main upwards to the left, which is to say in a beam that is mirror symmetrical to the central beam 34. The norm 32 shows the symmetrical axis.

Both test heads 20, 22 are operated in accord with the pulse echo principle. They emit ultra sound impulses and receive the echoes of these impulses. To this end a transmitter 36 or respectively 38 and a receiver 40 or respectively 42 are fitted to each of the test heads 20, 22. This is shown in FIG. 1. By means of a line 44 to which reference will be made later, the receiver 42 of the test head 22 from which the pulses are emitted vertically is connected to the receiver 40 of the test head 20 from which the pulses are emitted diagonally in order to activate the gate tier the expected error value in the receiver 40 of the test head from which the pulses are emitted diagonally. To this too reference will be made later.

Figure 2:
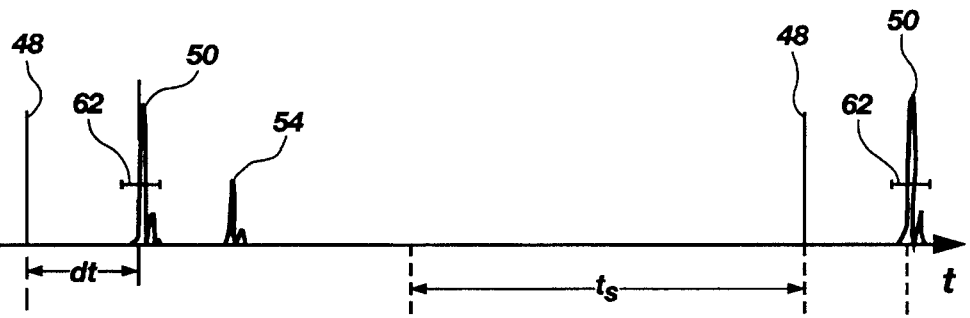
FIG. 2 shows for the test head on which the pulse impinges vertically and which is constructed in accord with FIG. 1 a time impulse diagram of the voltage U at the input component over the time range t.
Figure 3:
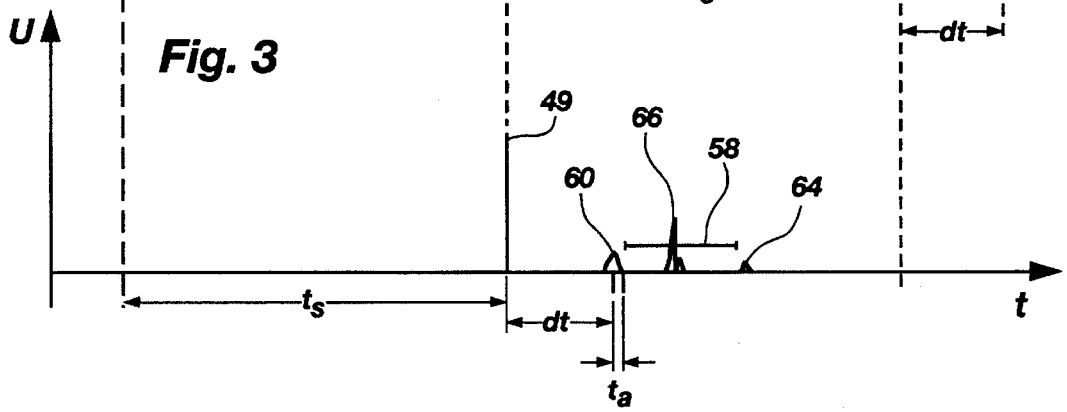
FIG. 3 shows, in a time range that is the same as for FIG. 2, a diagram for the test head from which the pulse is emitted diagonally and which is in accord with FIG. 2.

In the following the impulse processes that are in accord with FIG. 2 and FIG. 3 are described. A cycle provider 445, as is evident from FIG. 2, transmits at set intervals periodic impulses 48, 49 that are conducted alternately to the receiver of the test head from which pulses are emitted diagonally 36 and the receiver 38 of the test head from which pulses are emitted vertically where they at practically the same instant give rise to an ultra sound impulse (not shown). This impulse passes through the forward run (which is here not defined more exactly) and along the central beam to the surface 28 of the test piece 24. There a portion of the sound energy is reflected. The remainder enters the test body 24. The reflected amount produces the first activating cyclical signal 48 and subsequently the echo that follows the transmitted impulse. In the case of diagram FIG. 2, which describes the relationships for a test head 22 from which the pulses are emitted vertically, the entry echo 50 follows at an instant dt subsequent to the instant that marks the triggering instant in the cycle 48. If there is in the test body 24 no reflector of any kind, the coupled sound pulse proceeds further to the back wall 52, where a portion of it at least is reflected; and in its turn a portion of the echo from the rear wall proceeds to the test head 22, where it gives rise to a rear wall echo 54. The time difference between the entry echo 50 and the rear wall echo 54 can be utilized in the well known manner in order to determine the thickness of the material (and also the thickness of the wall) of the test body 24. In this connection attention is drawn once again to the publication DE 38 22 699 At. But for the process that is here described the entry echo 50 is important.

The entry echo 50, which is to say the first echo that, following the transmitted pulse, is registered in the receiver 42, is processed in a circuit arrangement 56 (see FIG. 1 ) and delayed. This circuit arrangement 56 is incorporated in the wire 44 and therefore conducted to the receiver 40 of the test head from which the pulses are emitted diagonally 20. Here it is employed to trigger the expected error gate 58.

In the model described, pulse 49, which follows the pulse 48 and which is transmitted at an instant that is a whole number multiplication of the cyclical time $T_s$ following the cyclical impulse 48 from the cyclical impulse trigger 46, triggers a transmitted pulse after the beat 48 from the cyclical trigger 46 of the test head 20 from which the pulses are emitted diagonally. In this way an ultra sound impulse traverses the central beam 34, and part of it enters through an area around the point 30 the test body 24 while another portion gives rise to a reflection. A small portion of the reflected pulse appears as a weak input echo. In accordance with the available technology, this input echo 60 is utilized to activate the expected error gate 58. In the process described here, however, this input echo 60 is ignored. Instead, the expected error gate 58 is activated by a signal from the circuit arrangement 56 that is generated at an instant dt following the cyclical impulse 49. In this arrangement the time dt is, as described above, the elapsed time between the cyclical impulse 48 and the input entry echo 50. In an improved version the time dt will be the varying mean value between the last n time differences between each cyclical pulse 48 that activates the test head 22 and the instant of the input entry echo 50, or it will constitute a different processing of several values.

The entry echo 50 is evaluated and processed in the circuit arrangement 56 in order to ascertain the time dt. Measuring the time for dt is for example stopped when the first leading edge of an input entry echo 50 consisting of several half waves exceeds a given threshold value 62. In yet another version the instant of greatest amplitude of the input entry echo 50 can also be utilized for terminating the measurement of dt. Publication DE 35 19 797 AI describes a process whereby from an input echo that frequently consists of several half waves a signal for terminating the measuring of dt can be deduced.

In the version described here the forward runs for both test heads 20, 22 are of the same dimensions. The forward runs are also identical in terms of their physical properties. In consequence, following the triggering instant 48, 49, an ultra sound impulse requires for both test heads 20, 22 the same amount of time to reach point 30 on the surface 28. In this case the time gate 58 (the expected error gate) in the receiver 40 of the test head from which pulses are emitted diagonally 20 is activated at an instant dt following the cyclical signal 49, and the actual expected error gate 58 then is activated following an additional time delay $t_a$, which can be adjusted and which takes account of the decline in the input echo 60 so that this does not proceed into the expected error gate 58. This is shown in FIG. 3. The end of the expected error gate 58 is of no consequence for this description, as the expected error gate 58 in the version here described ends at sufficient distance from the rear wall echo 64 that this too in its turn does not enter the expected error range. The echo 66 of an imperfection 68 in the test body 24 falls in the expected error range.

In the event that the forward runs for each of the test heads 20, 22 are not identical an appropriate constant period of time $t_4$ is introduced, and the expected error gate 58 is then activated at the instant dt+$t_v$, following the triggering cyclical pulse 49.

If the distance between the test head from which pulses are emitted vertically 22 and the surface 28 of the test body 24 changes the time period dt changes. Within the range of certain small changes it is not necessary to "take account of this influence. But if the change exceeds a certain threshold a correction must be made. Point of departure for this correction is the distance given when justifying the device. Should this distance exceed a certain amount the expected error gate can be activated at the wrong instant; it can be started too early or too late. To avoid this it is proposed in a subsequent development of the device to incorporate in the circuit arrangement 56 some compensation for the altered run. To this end the increment by which the time span dt at the time of justification was changed will be taken into account. The increment can be positive or negative. It is multiplied by a geometry factor which in essence is a trigonometric function of the input angle. In this way compensation is effected for the longer pre run for the test head 20. It is longer because the pulses impinge vertically, with respect to changes in the distances between the test head 22 and the surface 28.

We claim:

1. A process for activating a time gate in an ultrasonic testing device for inspection of a test body utilizing pulse reflection techniques, comprising the steps of:

applying ultrasonic pulses originating from a first test head to a surface of the test body at normal incidence to said surface;

receiving pulses reflected from said surface with said first test head and evaluating an entry echo therefrom;

applying ultrasonic pulses originating from a second test head to the surface of the test body at oblique incidence to the said surface, whereby said second test head is firmly connected to said first test head and the first and the second test head transmit pulses cyclically and at given intervals;

receiving all pulses reflected from the test body relating to said obliquely applied pulses with said second test head and evaluating only those pulses received which are in said time gate; and establishing a sliding chronological mean value of the entry echoes of several ultrasonic pulses originating from the first test head and utilizing the sliding chronological mean value obtained in each instance to activate the time gate.

2. A process as set forth in claim 1 wherein the entry echo is composed of several half waves which have different amplitudes, and wherein the very half wave having the greatest amplitude is utilized for establishing the sliding chronological mean value.

3. A process as set forth in claim 1, wherein the entry echo is composed of several half waves and wherein always the same half wave, namely the n-th half wave is utilized for establishing the sliding chronological mean value.

4. An apparatus for activating a time gate in an ultrasonic testing device for inspection of a test body utilizing pulse reflection techniques, comprising:

a first test head for applying ultrasonic pulses originating therefrom to a surface of the test body at normal incidence to said surface and receiving pulses reflected from said surface;

means for detecting the pulses reflected from said surface relating to said first test head and for evaluating an entry echo from the pulses;

a second test head for applying ultrasonic pulses originating therefrom into the test body at oblique incidence to said surface and receiving pulses reflected from at least one error in the test body;

means for firmly connecting the first test head and the second test head and for moving the first test head and the second test head relative to the test body:

means for controlling the first test head and the second test head to emit pulses cyclically and at given intervals;

means for detecting the pulses reflected from the at least one error in the test body including the time gate, so that only those pulses reflected from at least one error in the test body are further processed which are in the time gate; and means for establishing a sliding chronological mean value of the entry echoes of several ultrasonic pulses originating from the first test head and utilizing the sliding chronological mean value obtained in each instance to activate the time gate.

5. An apparatus as set forth in claim 4 further comprising means for detecting a half wave of the entry echo having the greatest amplitude, and utilizing this half wave for establishing the sliding chronological mean value.

6. An apparatus as set forth in claim 4, further comprising means for detecting a specific half wave of the entry echo, namely the n-th half wave and utilizing this half wave for establishing the sliding chronological mean value.

* * * * *